United States Patent [19]

Arlt

[11] 4,138,452

[45] Feb. 6, 1979

[54] PROCESS FOR PREPARING PHOSPHORIC ACID ESTERHALIDES

[75] Inventor: Dieter Arlt, Cologne, Fed. Rep. of Germany

[73] Assignee: Bayer Aktiengesellschaft, Leverkusen, Fed. Rep. of Germany

[21] Appl. No.: 857,154

[22] Filed: Dec. 5, 1977

Related U.S. Application Data

[63] Continuation of Ser. No. 654,670, Feb. 2, 1976, abandoned.

[30] Foreign Application Priority Data

Feb. 22, 1975 [DE] Fed. Rep. of Germany ....... 2507779

[51] Int. Cl.² .............................. C07F 9/14; C07F 9/42
[52] U.S. Cl. ..................................... 260/955; 260/960
[58] Field of Search ............................. 260/960, 955

[56] References Cited

U.S. PATENT DOCUMENTS 3,980,738  9/1976  Arlt .............................. 260/963 XR

*Primary Examiner*—Anton H. Sutto
*Attorney, Agent, or Firm*—Sprung, Felfe, Horn, Lynch & Kramer

[57] ABSTRACT

A phosphoric acid esterchloride is prepared by simultaneously reacting a phosphoric acid ester of formula I

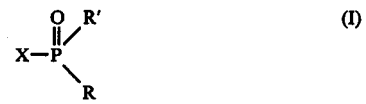

wherein
R is alkoxy with 1 - 8 carbon atoms optionally substituted by halogen, and
R' is $C_1$-$C_8$ alkoxy radical, optionally substituted by halogen, or is chlorine, bromine fluorine or $C_1$-$C_6$ alkyl or phenyl, each optionally substituted by halogen, and
X is fluorine, chlorine or bromine,
with a halogenating agent and an olefin of formula II

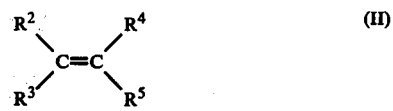

wherein
$R^2$ and $R^4$ are the same or different and each is hydrogen, halogen or straight-chain or branched optionally substituted $C_1$-$C_{18}$ alkane, $C_1$-$C_6$ acyloxy or $C_2$-$C_{12}$ alkenyl, or phenyl optionally substituted by halogen and/or by $C_1$-$C_4$ alkyl and $R^4$ may be, in addition, chlorocarbonyl, nitrile, carbalkoxy or optionally N-substituted carbamino containing in each case, up to 9 carbon atoms, alkylcarbonyl alkylsulphonyl, arylcarbonyl or arylsulphonyl containing, in each case, up to 7 carbon atoms or an aldehyde group, or the radicals $R^2$ and $R^4$ are joined together to form a 4-membered to 12-membered, carbocyclic or heterocylic ring, and $R^3$ and $R^5$ are the same or different and each is hydrogen, halogen or $C_1$-$C_4$ alkyl.

9 Claims, No Drawings

PROCESS FOR PREPARING PHOSPHORIC ACID ESTERHALIDES

BACKGROUND

This is a continuation, application Ser. No. 654,670, filed Feb. 2, 1976 now abandoned.

This invention relates to a process for the preparation of phosphoric acid ester-halides and to phosphoric acid ester-halides obtainable with the aid of this process.

It is known to prepare phosphoric acid ester-chlorides by selective reaction of phosphoryl chloride with alcohols (compare Houben-Weyl XII/2, page 212 (1964)). The disadvantage of this process is that only a limited number of alcohols, especially primary alcohols, can be used as the starting material. Thus, the preparation of substituted compounds is correspondingly restricted and in certain cases, for example for phosphoric acid alkyl ester-halides halogenated in the 1-position in the alkyl radical, can be achieved in a controlled manner at best via a multi-stage reaction sequence.

SUMMARY

A process for the preparation of phosphoric acid ester-chlorides has now been found which is characterized in that a phosphoric acid ester of the general formula I

in which the radical

R represents an alkoxy radical with 1-8 carbon atoms, which is optionally substituted by halogen and R' represents a $C_1$-$C_8$ alkoxy radical, which is optionally substituted by halogen, or represents chlorine, bromine, fluorine or a $C_1$-$C_6$ alkyl or phenyl radical, which is optionally substituted by halogen, and X represents fluorine, chlorine or bromine, is reacted simultaneously with a halogenating agent and an olefine of the general formula II

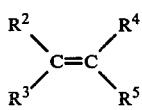

in which the radicals $R^2$ and $R^4$ are identical or different and represent hydrogen, halogen or a straight-chain or branched, optionally substituted $C_1$-$C_{18}$ alkane, $C_1$-$C_6$ acyloxy or $C_2$-$C_{12}$ alkenyl radical, substituents which may be mentioned being halogen, acyloxy or alkoxy groups with 1-18 carbon atoms, the isocyanate group, the isocyanide-dichloride groups, the chlorocarbonyl group, the nitrile group or the chlorosulphone group, a carbalkoxy group with 1-8 carbon atoms in the alcohol radical or an optionally substituted carbamino group with up to 12 carbon atoms in the molecule, and also represent a phenyl radical which is optionally substituted by halogen and/or by $C_1$-$C_4$ alkyl groups and the radical $R^4$ also represents, in addition to the abovementioned groups, the chlorocarbonyl or nitrile group or a carbolkoxy radical or a carbamino radical, which is optionally substituted on the nitrogen atom, with, in each case, up to 9 carbon atoms in the molecule, or represents an alkylcarbonyl, an alkylsulphonyl, an arylcarbonyl or an arylsulphonyl group with, in each case, up to 7 carbon atoms in the molecule or represents the aldehyde group and optionally the radicals $R^2$ and $R^4$ conjointly are, as a result of an additional bond between the radicals $R^2$ and $R^4$, a constituent of a 4-membered to 12-membered, preferably 5-membered or 6-membered, carbocyclic or heterocyclic ring, oxygen, sulphur or nitrogen preferably occurring as hetero-atoms, and $R^3$ and $R^5$ are identical or different and represent hydrogen, halogen or a $C_1$-$C_4$ alkyl radical.

Preferred phosphoric acid esters, according to the general formula I, which may be mentioned are those in which R represents a $C_1$-$C_6$ alkoxy radical, preferentially the methoxy and the ethoxy radical, and R' represents a $C_1$-$C_4$ alkoxy radical or represents a $C_1$-$C_3$ alkyl radical, chlorine, bromine, fluorine or the phenyl radical and preferentially represents the methoxy, ethoxy, propoxy, isopropoxy, methyl or ethyl radical and X represents chlorine.

DESCRIPTION

Examples which may be mentioned are: phosphoric acid dimethyl ester-monochloride, phosphoric acid diethyl ester-monochloride, phosphoric acid diethyl ester-monobromide, phosphoric acid dimethyl ester-monofluoride, phosphoric acid dibutyl ester-monochloride, phosphoric acid monomethyl ester-dichloride, phosphoric acid monoethyl ester-dichloride, phosphoric acid monoethyl ester-difluoride, phosphoric acid mono-(2-chloroethyl) ester-dichloride, phosphoric acid monoisopropyl ester-dichloride, phosphoric acid monopropyl ester-dichloride, methanephosphoric acid monomethyl ester-chloride, ethanephosphonic acid monoethyl ester-chloride and phenyl-phosphonic acid monomethyl ester-chloride.

The phosphoric acid esters which are used for the process according to the invention are known and can be prepared by reacting the corresponding phosphoric acid chlorides such as, for example, phosphoryl chloride, with the appropriate alcohols (compare Houben-Weyl, Methods of Organic Chemistry, Volume XII, 2 page 211 (Stuttgart 1964)).

Preferred olefines, according to the general formula II, which may be mentioned are those in which $R^2$ and $R^4$ are identical or different and represent hydrogen, fluorine, chlorine, bromine or an optionally substituted $C_1$-$C_5$ acyloxy radical, a $C_1$-$C_6$ alkane radical or a $C_2$-$C_6$ alkenyl radical, substituents of these radicals which may be mentioned being chlorine, bromine, the isocyanate group, the isocyanide-dichloride group, the chlorocarbonyl group, the nitrile group or the chlorosulphonyl group, a carbalkoxy group, an acyloxy group or an alkoxy group with, in each case, 1-5, and preferentially 1-3, carbon atoms in the molecule, as well as a carbamino group which is preferably substituted on the nitrogen atom by methyl or ethyl, and $R^2$ preferentially represents fluorine, chlorine or bromine and $R^4$ has the abovementioned scope of meanings but does not represent fluorine, chlorine or bromine simultaneously with $R^2$.

Further preferred olefines which may be mentioned are those in which
R⁴ represents the chlorocarbonyl group, the nitrile group, a carbalkoxy group or a mono-alkylated or dialkylated carbamino group, with 1 to 5 carbon atoms in the molecule, an alkycarbonyl or alkylsulphonyl group with 1 to 4 carbon atoms in the molecule and also an arylcarbonyl or arylsulphonyl group, which preferably contains the phenyl radicals as the aryl radical, and preferentially the radicals $R^2$, $R^3$ and $R^5$ are identical or different and represent hydrogen, chlorine, bromine or a $C_1$–$C_6$ alkane radical and at least one of the radicals $R^2$, $R^3$ and $R^5$ represents hydrogen.

Examples which may be mentioned of olefines which are used for the process according to the invention are: branched and unbranched alkenes, especially ethylene, propylene, but-1-ene and but-2-ene, isobutene, hex-1-ene, dodec-1-ene, tri- and tetra-propylene, tetraisobutene, oct-1-ene, octadec-1-ene, 1-phenyl-3,3,4,4,-tetrafluoro-cyclo-butene, cyclopentene, cyclohexene, cyclooctene, cyclododecene, styrene, α-methylstyrene, α- and β-pinene and camphene; diolefines, especially buta-1,3-diene, isoprene, 2,3-dimethyl-buta-1,3,-diene, vinylcyclohexene and cyclooacta-1,4,-diene; halogenated olefines, such as allyl chloride, methallyl chloride and vinyl chloride, 1- and 2-chloropropene, 1,4- and 3,4-dichloro-but-2-ene, vinyl bromide and allyl bromide, vinyl fluoride, 1,1-dichloroethylene, 1,1-difluoroethylene and trifluoromonochloroethylene, 1-chlorocyclohexene and 3-chloro-cyclohexene; esters, mono- and dialkylamides, chlorides and nitriles of unsaturated carboxylic acids, especially of acrylic acid, methacrylic acid, crotonic acid, β,β-dimethyl-acrylic acid, β-chloroacrylic acid, β,β-dichloroacrylic acid, vinylacetic acid, undecenecarboxylic acid, oleic acid, linoleic acid, cyclohexene-1-carboxylic acid and cyclohexene-3-carboxylic acid, maleic acid, itaconic acid and fumeric acid; esters and ethers of unsaturated alcohols, especially of allyl alcohol, butene-1,4-diol and methylenepropane-1,3-diol, for example ethyl vinyl ether, butyl vinyl ether, vinyl acetate and isopropenyl acetate and 1,3-dioxolen-2-one; isocyanates and isocyanide-dichlorides with olefinic groupings, especially allyl isocyanate and allyl isocyanide-dichloride, 4-chloro-butenyl isocayanate and 4-chlorobutenyl isocyanide-dichloride and isopropenyl isocyanate; ketones and sulphones with olefinic groupings, especially methyl vinyl ketone, mesityl oxide, phenylvinyl-sulphone, sulpholene and 3-methylsulpholene; and olefinic sulphonic acid derivatives, especially β-chloro-vinyl-, allyl- and methylallyl-, vinyl- and β,β-dimethylvinyl-sulphonyl chloride.

Very particularly preferred olefines are those according to the general formula, in which
$R^2$ and/or $R^3$ represent fluorine, chlorine or bromine, especially fluorine or chlorine, and $R^3$ also can represent hydrogen and
the radicals $R^4$ and $R^5$ in each case represent hydrogen, a $C_1$–$C_6$ alkane radical or the phenyl radical.

Examples which may be mentioned are: monofluoroethylene, monochloroethylene, monobromethylene, 1,1-difluoroethylene, 1,1-dichloroethylene, 1-fluoro-2-methylethylene, 1-fluoro-2-ethylethylene, 1-fluoro-2-phenylethylene, 1-chloro-prop-1-ene and 2-chloro-prop-1-ene.

The vinyl fluorides and vinylidene fluorides which are employed for the process according to the invention are known or can be prepared according to known processes, for example by an addition reaction of one molecule of HF with appropriate acetylenes or, respectively, of two molecules of HF with acetylenes, subsequent chlorination and dehydrochlorination.

The phosphoric acid ester-chlorides obtainable by the process according to the invention can be represented by the general formula III

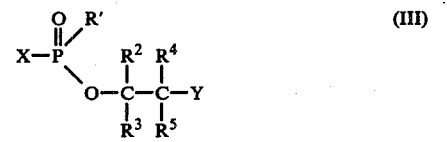

in which the radicals
R', $R_2$, $R_3$, $R_4$, $R_5$ and X have the same meaning as for the starting products of the general formula I or II respectively and
Y represents chlorine or bromine, in accordance with the halogenating agent used for the process according to the invention.

Examples which may be mentioned of phosphoric acid ester-halides, according to the general formula III, are:

| X | Y | R' | $R^2$ | $R^3$ | $R^4$ | $R^5$ |
|---|---|---|---|---|---|---|
| Cl | Cl | Cl | Cl | H | H | H |
| Cl | Cl | Cl | Br | H | H | H |
| Cl | Cl | CH₃ | Cl · | H | H | H |
| Cl | Cl | OCH₃ | Cl | H | H | H |
| Cl | Cl | OC₂H₅ | Cl | H | H | H |
| Cl | Br | OC₃H₇ | Cl | H | H | H |
| Cl | Cl | Cl | CH₃ | H | CH₃ | H |
| Cl | Br | OCH₃ | CH₂Cl | H | H | H |
| Cl | Cl | Cl | —CH=CH₂ | H | H | H |
| Cl | Cl | OC₃H₇ | C₆H₅ | H | H | H |

New compounds, which are obtainable with the aid of the process according to the invention and which may be mentioned are:
Compounds of the general formula III, in which
X represents fluorine, chlorine or bromine, Y represents chlorine or bromine,
R' represents a $C_1$–$C_8$ alkyl radical or phenyl radical, which are optionally substituted by halogen, and $R^2$ and $R^4$ are identical or different and represent hydrogen, halogen or a straight-chain or branched, optionally substituted $C_1$–$C_{18}$ alkane, $C_1$–$C_6$ acyloxy or $C_2$–$C_{12}$ alkenyl radical, substituents which may be mentioned being halogen, acyloxy or alkoxy groups with 1 –18 carbon atoms, the isocyanate group, the isocyanide-dichloride group, the chlorocarbonyl group, the nitrile group or the chlorosulphone group, a carbalkoxy group with 1-8 carbon atoms in the alcohol radical or an optionally substituted carbamino group with up to 12 carbon atoms in the molecule, and also represent a phenyl radical which is optionally substituted by halogen and/or by $C_1$–$C_4$ alk groups and the radical $R^4$ also represents, in addition to the abovementioned groups, the chlorocarbonyl or nitrile group or a carbalkoxy radical or a carbamino radical, which is optionally substituted on the nitrogen atom, with, in each case, up to 9 carbon atoms in the molecule, or represents an alkylcarbonyl, an alkylsulphonyl, an arylcarbonyl or an arylsulphonyl group with, in each case, up to 7 carbon atoms in the molecule or represents the aldehyde group and optionally the radicals $R^2$ and $R^4$ conjointly are, as a result of an additional bond between the radicals $R^2$ and $R^4$, a constituent of a 4-membered to 12-membered, preferably 5-membered or 6-membered, carbocyclic or heterocyclic ring, oxygen, sulphur or nitrogen preferably occurring as hetero-atoms, and $R^3$ and $R^5$ are identical or different and represent hydrogen, halogen or a $C_1$-$C_4$ alkyl radical, and also compounds of the general formula III, in which X represents fluorine, chlorine or bomine, Y represents chlorine or bromine, R' represents a $C_1$-$C_8$ alkoxy radical, which is optionally substituted by halogen, or represents fluorine, chlorine or bromine, $R^2$ represents fluorine, $R^3$ represents fluorine or hydrogen and $R^4$ and/or $R^5$ represents hydrogen, $C_1$-$C_4$ alkyl or phenyl.

The compounds listed in Table 1 may be mentioned by way of example:

Table 1

| X | Y | R' | $R^2$ | $R^3$ | $R^4$ | $R^5$ |
|---|---|---|---|---|---|---|
| F | Cl | CH₃O | F | F | H | H |
| Cl | Cl | CH₃O | F | F | H | H |
| Cl | Br | CH₃O | F | F | H | H |
| Cl | Cl | CH₃O | F | H | H | H |
| Cl | Cl | C₂H₅O | F | H | H | H |
| Cl | Cl | Cl | F | F | H | H |
| Cl | Br | Cl | F | F | H | H |
| Cl | Cl | Cl | F | H | H | H |
| Cl | Br | Cl | F | H | H | H |
| F | Cl | F | F | H | H | H |
| Br | Cl | Br | F | H | H | H |
| Cl | Cl | CH₃ | F | H | H | H |
| Cl | Br | CH₃ | F | H | H | H |
| Cl | Cl | C₂H₅ | F | H | H | H |
| Cl | Cl | C₃H₇ | F | H | H | H |
| Cl | Cl | C₆H₅ | F | H | H | H |

Elementary halogen, especially chlorine or bromine, can be used as the halogenating agent for the process according to the invention. Of course, compounds which split off chlorine or bromine under the reaction conditions, for example sulphuryl chloride, can also be employed.

The reaction temperature for the reaction according to the process of the invention is not in itself critical and can vary within wide limits. In general, the reaction is carried out at between $-50$ and $+120°$ C., appropriately between about $-10$ and $+100°$ C. and preferably at $-10$ to $+50°$ C.

In general, the reaction is carried out under normal pressure.

The process according to the invention is preferably carried out in the presence of solvents or diluents. Solvents and diluents which can be used are organic solvents which are inert towards the reactants, such as, for example, aliphatic and aromatic chlorinated hydrocarbons, dichloromethane, chloroform, chlorobenzene or dichlorobenzene but also an excess of the particular phosphoric acid ester-halide, in so far as this is liquid under the reaction conditions.

In some cases it has also proved advantageous to add a small amount of Friedel-Crafts catalysts, especially, for example, iron-(III) chloride, zinc chloride or aluminum chloride, to the reaction mixture.

In order to achieve good yields, the process according to the invention is appropriately carried out using equivalent amounts of halogenating agent and at least equivalent amounts of the phosphoric acid ester-halide employed as the starting material, these amounts being based on the olefine. In general, particularly good results are obtained when the phosphoric acid ester-halide employed is used in excess, for example in a molar ratio of 1 : 1 to 5 : 1, based on olefine employed.

Using, as an example, the reaction of phosphoric acid monomethyl ester-dichloride with vinyl chloride as the olefine and chlorine as the halogenating agent, the process according to the invention can be illustrated in more detail by the equation which follows:

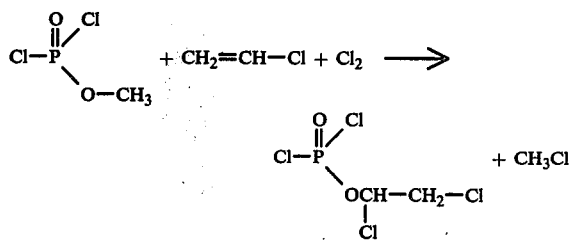

When the phosphoric acid ester used as the starting material contains two alkoxy groups as the substituents R and R', the reaction according to the process of the invention can be continued stepwise, when an appropriate excess of olefine and halogenating agents are present, by substitution of both alkoxy groups to give two new phosphoric acid diestermonochlorides, as is illustrated in more detail by the equation which follows, using, as an example, the reaction of phosphoric acid dimethyl ester-monochloride with vinyl fluoride as the olefine and chlorine as the halogenating agent.

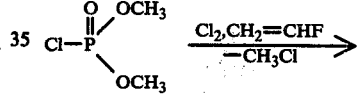

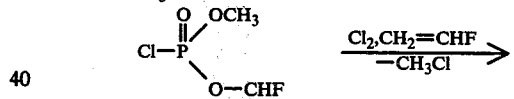

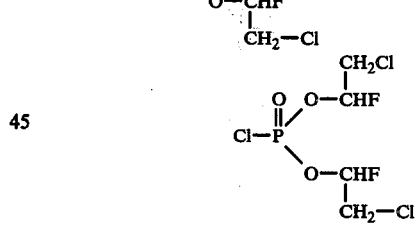

In this case the phosphoric acid ester-halide obtainable as the product contains, in place of the radical R', the radical

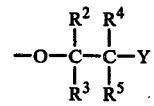

In order to carry out the process according to the invention in practice it is appropriate initially to introduce the phosphoric acid ester-halide employed, if necessary in an inert solvent or diluent, and to add the halogenating agent and the olefine simultaneously to this solution at the indicated temperatures, the internal temperature of the mixture being regulated by external cooling. After the reaction has subsided, the batch is stirred for a further period whilst warming (preferably at 40 to 100° C.) in order to carry the reaction to completion. The reaction mixture is then cooled to room temperature and worked up according to customary methods, for example by fractional vacuum distillation.

The products obtainable according to the process of the invention are generally obtained in the form of colourless to pale yellow coloured oils, which are insoluble in water and which generally can be distilled without decomposition under reduced pressure and can be purified in this way. when mixtures of different iosmers are obtained as the product, these can be separated by fractional distillation.

An advantage of the process according to the invention is that the preparation of known phosphoric acid ester-chlorides is considerably simplified and numerous new compounds of this type, which cannot be prepared according to methods known hitherto, are accessible.

A further advantage is that the process according to the invention has universal applicability and can be carried out industrially in a simple manner and that the requisite starting materials are readily accessible. The high purity and good yields of the products obtainable by the process according to the invention is also advantageous.

The phosphoric acid ester-chlorides which can be prepared according to the process of the invention serve as intermediate products for the preparation of insecticides and flameproofing agents (see U.S. Pat. No. 2,947,773/Table 1).

EXAMPLE 1

55 g of vinyl fluoride and 70 g of chlorine are simultaneously passed into 308 g of phosphoric acid dimethyl ester-monochloride $(CH_3O)_2POCl$ at $-5°$ C. to $0°$ C., whilst stirring and cooling. After the reaction has taken place, the mixture is first degassed in vacuo at room temperature and then is subjected to fractional distillation. 143 g (=69% of theory) of phosphoric acid 0-methyl-0-(2-chloro-1-fluoro-ethyl) ester-monochloride of the formula $Cl-PO(OCH_3)(OCHF-CH_2Cl)$ which has a boiling range b.p.$_{0.3}$: 69° – 72° C., and 11 g (=8% of theory) of phosphoric acid di-(2-chloro-1-fluoroethyl) ester-monochloride of the formula $Cl-PO(OCHF-CH_2Cl)_2$ which has a boiling range b.p.$_{0.2}$: 85° – 90° C., are obtained.

EXAMPLE 2

The reaction is carried out analogously to Example 1, using 600 g of $(CH_3O)_2POCl$, 195 g of $Cl_2$ and 140 g of vinyl fluoride, instead of the amounts indicated in Example 1. In this case 307 g (52% of theory) of the compound $Cl-PO(OCH_3)(OCHF-CH_2Cl)$ and 72 g (=21.5%) of the compound $Cl-PO(OCHF-CH_2Cl)_2$ are obtained.

EXAMPLE 3

71 g of chlorine and 90 g of vinyl chloride are passed into 172 g of phosphoric acid diethyl ester-monochloride $Cl-PO(OC_2H_5)_2$. The temperature is kept at about 0° C. by cooling. The reaction mixture is warmed to 50° C. in order to remove ethyl chloride and is then subjected to fractional distillation in vacuo. 105 g (=43.5% of theory) of phosphoric acid 0-ethyl-0-(1,2-dichloroethyl) ester-monochloride of the formula $Cl-PO(OC_2H_5)(OCHCl-CH_2Cl)$, which has a boiling point b.p.$_{0.1}$ : 72° C., and 52 g (= 33.4% of theory) of phosphoric acid di-(1,2-dichloroethyl) ester-monochloride $Cl-PO(OCHCl-CH_2Cl)_2$, which has a boiling point b.p.$_{0.1}$ : 110° C., are obtained.

EXAMPLE 4

70 g of vinyl fluoride are passed into 212 g of $Cl-PO(OCH_3)_2$ at about 0° C., whilst stirring and cooling, 117 g of bromine being added dropwise at the same time. The mixture is then degassed under a waterpump vacuum and subjected to fractional distillation. 120 g (−65% of theory) of phosphoric acid 0-methyl-0-(2-bromo-1-fluoroethyl) ester-monochloride of the formula $Cl-PO(OCH_3)(OCHF-CH_2Br)$, which has a boiling range b.p.$_{0.2}$:80°–83° C., and 14 g of the compound $Cl-PO(OCHF-CH_2Br)_2$, which has a boiling range of 100° – 105° / 0.15 mm Hg, are obtained.

EXAMPLE 5

20 g of chlorine and 20 g of vinyl fluoride are passed into 20 g of phosphoric acid monopropyl ester-di-chloride $Cl_2PO-O-nC_3H_7$ at $-10°$ C. to $0°$ C. 20.2 g (=85% of theory, based on phosphoric acid propyl ester-dichloride employed) of phosphoric acid (2-chloro-1-fluoroethyl) ester-dichloride of the formula $Cl_2PO-OCHF-CH_2Cl$, which has a boiling range of 46° – 48° C./0.2 mm Hg, are obtained by fractional distillation.

EXAMPLE 6

30 g of vinyl fluoride and 40 g of chlorine are passed into 80 g of phosphoric acid monoethyl ester-dichloride at about 0° C. After working up the fractional distillation, 75 g (=77.5% of theory, based on phosphoric acid ethyl ester-chloride employed) of the compound $Cl_2PO-O-CHF-CH_2Cl$, which has a boiling range of 43°–46° C./0.1 mm Hg, are obtained.

EXAMPLE 7

20 g of vinyl chloride and 20 g of chlorine are passed into 20 g of phosphoric acid monopropyl ester-dichloride, the reaction temperature being kept between 0° C. and +10° C. by cooling. Working up by the distillation gives 16g (=62.5% of theory) of phosphonic acid (1,2-dichloroethyl) ester-dichloride, which has a boiling range of 56°–60° C./0.1 mm Hg.

EXAMPLE 8

80 g of vinyl bromide are added dropwise to 80 g of phosphoric acid monoethyl ester-dichloride at −5° C. to 0° C., 45 g of chlorine being passed in simultaneously and the heat of reaction being compensated by a cooling bath. 52 g (=40% of theory) of the compound $CH_2Cl-CHBr-O-POCl_2$, which has a boiling range of 66°–68° C./0.1 mm Hg, obtained by fractional distillation of the resulting product mixture.

EXAMPLE 9

100 g of chlorine and 65 g of vinyl fluoride are simultaneously introduced into 135 g of ethane phosphonic acid ethyl ester chloride. The temperature is kept at between −10° C. and 0° C. by means of cooling. After working up by fractional distillation, 120 g (=67% of the theory) of ethane phosphonic acid (2-chloro-1-fluoroethyl ester) chloride, which has a boiling range of 65–67° C./0.2 mm Hg, are obtained.

EXAMPLE 10

60 g of chlorine, 39 g of vinylidene fluoride and in addition 0.5 g of $FeCl_3$ are introduced into 67 g of phosphoric acid methyl ester dichloride. The temperature is kept at 10 to 20° C. by means of cooling. After working up by fractional distillation in vacuo, 75 g (75% of the theory) of phosphoric acid (2-chloro-1,1-difluoro-ethyl ester)-dichloride, which has a boiling range of 45–50° C./4 mm Hg, are obtained.

What is claimed is:

1. Compound of the formula

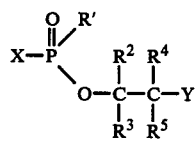 (III)

wherein
X is chlorine or bromine;
Y is chlorine or bromine;
$R^1$ is $C_1$–$C_8$ alkoxy, $C_1$–$C_8$ haloalkoxy, fluorine, chlorine or bromine;
$R^2$ is fluorine;
$R^3$ is hydrogen, fluorine, chlorine or $C_1$–$C_4$ alkyl; and
$R^4$ and $R^5$, which may be identical or different, are hydrogen, $C_1$–$C_4$ alkyl, or phenyl.

2. A compound according to claim 1 having the formula

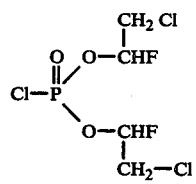

3. A compound according to claim 1 having the formula

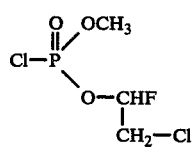

4. A compound according to claim 1 having the formula

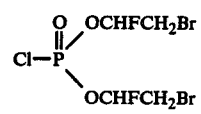

5. A compound according to claim 1 having the formula

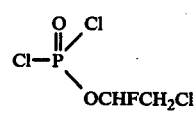

6. A compound according to claim 1 having the formula

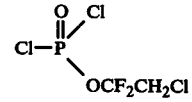

7. A compound according to claim 1 having the formula

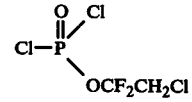

8. A compound according to claim 1 having the formula

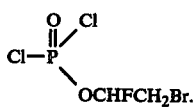

9. A compound according to claim 1 having the formula

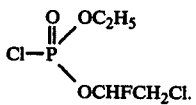

* * * * *

UNITED STATES PATENT AND TRADEMARK OFFICE
CERTIFICATE OF CORRECTION

PATENT NO. : 4,138,452
DATED : February 6, 1979
INVENTOR(S) : ARLT

It is certified that error appears in the above-identified patent and that said Letters Patent are hereby corrected as shown below:

Column 1, line 12, "bv" should read -- by --.

Column 1, line 68, "carbolkoxy" should read -- carbalkoxy --.

Column 2, line 39, "methanephosphoric" should read -- methanephosphonic --.

Column 3, line 6, "alkycarbonyl" should read -- alkylcarbonyl--.

Column 3, line 38, "fumeric" should read -- fumaric --.

Column 7, line 10, "when" should read -- When --.

Column 7, line 10, "iosmers" should read -- isomers --.

Column 7, line 34, "phosphoric" should read -- phosphonic --.

Column 7, line 53, "-$CH_2$Cl)" should read -- -$CH_2$-Cl) --.

Column 8, line 30, insert -- by -- after "up" and delete "the" after "up".

Signed and Sealed this

Seventeenth Day of July 1979

[SEAL]

Attest:

LUTRELLE F. PARKER
*Attesting Officer*     *Acting Commissioner of Patents and Trademarks*